(12) United States Patent
Wu et al.

(10) Patent No.: US 6,355,831 B1
(45) Date of Patent: Mar. 12, 2002

(54) PROCESS FOR PREPARING PENTENOIC ESTERS FROM FORMYLVALERIC ESTERS USING A MIXED OXIDE SUPPORTED NOBLE METAL CATALYST

(75) Inventors: Kuo-Ching Wu; Wen-Chyi Lin, both of Hsinchu; Po-Yu Chen, Taoyuan Hsien, all of (TW)

(73) Assignees: Industrial Technology Research Institute, Hsinchu; Acelon Chemicals & Fiber Corporation, Chang-Hua, both of (TW)

( * ) Notice: Subject to any disclaimer, the term of this patent is extended or adjusted under 35 U.S.C. 154(b) by 0 days.

(21) Appl. No.: 09/494,423

(22) Filed: Jan. 31, 2000

(30) Foreign Application Priority Data

Jul. 21, 1999 (TW) .......................................... 88112374 A

(51) Int. Cl.⁷ ........................... C07C 67/30; C07C 67/33
(52) U.S. Cl. ....................................................... 560/211
(58) Field of Search ........................................... 560/211

(56) References Cited

U.S. PATENT DOCUMENTS

| 4,879,405 A | * 11/1989 | Naeumann et al. |
| 4,879,406 A | * 11/1989 | Merger et al. |
| 5,962,680 A | * 10/1999 | Eisenschmid et al. |

* cited by examiner

*Primary Examiner*—Gary Geist
*Assistant Examiner*—Robert W. Deemie
(74) *Attorney, Agent, or Firm*—Sughrue Mion, PLLC

(57) ABSTRACT

The present invention provides a process for preparing a pentenoic ester, comprising heating a 3-, 4-formylvaleric ester or mixtures thereof at 50° C. to 400° C. in the presence of a supported noble metal catalyst. The noble metal catalyst is supported on a mixed oxide $(M^1)_a(M^2)_b(M^3)_cP_dAl_e\,SiO_x$, wherein $M^1$ is an alkali metal, $M^2$ is an alkaline earth metal, $M^3$ is a Group IVB metal, a=0.5~1.5, b=0.2~0.8, c=0.2~0.8, d=2~8, e=3~10, and x is the stoichiometric value. By means of the specific supported catalyst of the present invention, the selectivity of the 3- and 4-pentenoic esters can be increased and that of the 2-pentenoic ester can be greatly decreased.

17 Claims, No Drawings

PROCESS FOR PREPARING PENTENOIC ESTERS FROM FORMYLVALERIC ESTERS USING A MIXED OXIDE SUPPORTED NOBLE METAL CATALYST

BACKGROUND OF THE INVENTION

1. Field of the Invention

The present invention relates to a process for preparing a pentenoic ester, and more particularly to a process for preparing a pentenoic ester by using a 3- and 4-formylvaleric ester as the starting material in the presence of a specific mixed oxide-supported noble metal as the catalyst.

2. Description of the Prior Art

The conventional process for synthesizing caprolactam involves first reacting butadiene, carbon monoxide, and an alcohol to form a pentenoic acid, which is hydroformylated to form a formylvaleric ester. Then, the formylvaleric ester is reacted to form a 6-aminocaproate by amination, which is then cyclized to form caprolactam.

In the above process, when the pentenoic ester is hydroformylated, three kinds of isomers, including 3-, 4-, and 5-formylvaleric esters, are formed. However, only 5-formylvaleric esters can be reacted to form 6-aminocaproates, and thus 15–20% of the formations are undesirable byproducts, including 3- and 4-formylvaleric esters. Many attempts have been proposed to turn 3- and 4-formylvaleric esters back to pentenoic esters via dehydrocarbonylation, which can be used to prepare caprolactam, thus saving the cost of the raw material. 3- and 4-formylvaleric esters can be reacted to three kinds of isomers including 2-, 3-, and 4-pentenoic esters via dehydrocarbonylation. 3- and 4-pentenoic esters can be effectively reacted to 5-formylvaleric esters via hydroformylation, which can further be reacted to caprolactam. However, 2-pentenoic esters are very difficult to hydroformylate and are reacted to peroxides with oxygen. The result is that the hydroformylation catalyst loses its activity. Therefore, it is very important to decrease the selectivity of 2-pentenoic esters and increase the selectivity of 3- and 4-pentenoic esters.

Theoretically, when an aldehyde is reacted to an olefin, a Group VIII noble metal such as Pd (palladium), Pt (platinum), and Rh (rhodium) can be used as the catalyst.

J. Amer. Chem. Soc. 90 (1968), 94–98 discloses that n-decanal (an aldehyde) can be converted in the presence of palladium or platinum supported on active carbon to give olefins via dehydrocarbonylation. In addition, J. Amer. Chem. Soc. 90 (1968), 99–107 discloses that n-heptanal can be converted in the presence of rhodium complexes to give hexane by dehydrocarbonylation.

U.S. Pat. No. 4,517,400 describes that when palladium, platinum, or rhodium is present, the straight-chain aldehydes can be cleaved to give olefins, while the branched aldehydes show virtually no reaction.

German Pat. No. 1,917,244 describes a process for dehydrocarbonylating isobutyraldehyde using rhodium-containing alumina as a catalyst at 280° C., to 330° C.

European Patent Application No. 81,090 describes that formylvaleric esters, if heated to 150° C. to 600° C., undergo cyclization to 3,4-dihydro-2-pyrones.

In U.S. Pat. Nos. 4,879,405 and 4,879,406, 3- and 4-formylvaleric esters can be converted in the presence of a Group VIII noble metal as a catalyst at 50° C. to 400° C. to give pentenoic esters via dehydrocarbonylation. However, the total selectivity of the 2-pentenoic ester and valeric ester is higher than 20%, and the total yield of the 3- and 4-pentenoic esters is lower than 80%.

SUMMARY OF THE INVENTION

Therefore, the object of the present invention is to solve the above-mentioned problems and to provide a process for preparing a pentenoic ester by converting 3- and 4-formylvaleric esters. The yield of the pentenoic ester is higher than 85%, the selectivity of the 3- and 4-pentenoic esters is higher than 85%, and the selectivity of the 2-pentenoic ester can be greatly decreased.

To achieve the above-mentioned object, the process for preparing a pentenoic ester of the present invention includes heating a 3-, 4-formylvaleric ester or mixtures thereof at 50° C. to 400° C. in the presence of a supported noble metal catalyst.

One aspect of the present invention is that the noble metal catalyst is supported on a mixed oxide $(M^1)_a(M^2)_b(M^3)_c P_d Al_e SiO_x$, wherein $M^1$ is an alkali metal, $M^2$ is an alkaline earth metal, $M^3$ is a Group IVB metal, $a=0.5~1.5$, $b=0.2~0.8$, $c=0.2~0.8$, $d=2~8$, $e=3~10$, and x is the stoichiometric value.

In the above-mentioned mixed oxide, $M^1$ can be Li, Na, or K, $M^2$ can be Be, Mg, or Ca, $M^3$ can be Ti, Zr, or Hf. Preferably, $a=0.7–1.3$, $b=0.4–0.7$, $c=0.4–0.7$, $d=4–7$, and $e=4–8$.

Preferably, the noble metal catalyst used in the present invention contains a Group VIIIB metal, such as Pd (palladium), Pt (platinum), Rh (rhodium) or Ru (ruthenium).

DETAILED DESCRIPTION OF THE INVENTION

According to the present invention, the specific supported noble metal catalyst includes the noble metal catalyst itself and the mixed oxide $(M^1)_a(M^2)_b(M^3)_c P_d Al_e SiO_x$ as the support, which has two functions of dehydrocarbonylation and isomerization. In the presence of such a supported catalyst, 3- and 4-formylvaleric esters can undergo dehydrocarbonylation on the noble metal to give 2-, 3-, and 4-pentenoic esters. Then, the 2-pentenoic ester can be converted via isomerization on the mixed oxide support into 3- and 4-pentenoic esters. In this manner, the selectivity of the 2-pentenoic ester can be decreased. In addition, cyclization to 3,4-dihydro-2-pyrones from formylvaleric esters can be inhibited by means of the mixed oxide. Therefore, the mixed oxide can serve as a catalyst and has the properties of acid and base, which belongs to a solid acid/base catalyst.

The noble metal catalyst can be supported on the $(M^1)_a (M^2)_b(M^3)_c P_d Al_e SiO_x$ mixed oxide by ionic exchange, impregnation, or mechanical mixing. The noble metal catalyst to be supported can be in an amount of 0.01 to 10 wt %, preferably 0.1 to 5 wt %, based on the total weight of the noble metal catalyst and the mixed oxide support.

According to the present invention, the starting materials can be a 3-formylvaleric ester, 4-formylvaleric ester, or mixtures thereof. The starting materials are heated to a temperature of 50° C. to 400° C., preferably to 100° C. to 250° C., in the presence of the above-mentioned supported noble metal catalyst. In this way, the starting materials can be converted to a pentenoic ester via dehydrocarbonylation. The 3- and 4-formylvaleric esters can be independently an ester of alkyl, preferably an ester of alkyl having from 1 to 3 carbon atoms. Examples of alkyl are methyl, ethyl, propyl and isopropyl. Representative examples of the 3- and 4-formylvaleric esters include methyl 3-formylvalerate and methyl 4-formylvalerate.

The above-mentioned dehydrocarbonylation is preferably conducted in the presence of an oxygen-containing gas, such as air or oxygen. For example, 10–40% (in volume) of oxygen, which is diluted with an inert gas, can be introduced into the reactants. The inert gas can be nitrogen, carbon dioxide, helium, or argon.

Moreover, in order to minimize excess oxidation and byproduct generation, 0.01–10 wt % of water, based on the total weight of the formylvaleric esters, is preferably added to the starting materials. In addition, in order to avoid hydrolyzation of the formylvaleric esters and the pentenoic esters, alcohols, such as methanol, ethanol, butanol, or cyclohexanol, are preferably added to the starting materials. The alcohol is preferably in an amount of 30–90 wt % based on the total weight of the formylvaleric esters.

The liquid hour space velocity (LHSV) of the formylvaleric esters can be in a range of 0.1 to 10 $hr^{-1}$, preferably 0.5 to 5 $hr^{-1}$.

The conversion and selectivity mentioned in the present invention are calculated according to the following formulae, in which FV indicates formylvaleric ester and PTE indicates pentenoic ester:

conversion (mole%) =

$$\frac{\text{FV weight in the feedstock} - \text{FV weight in the product}}{\text{FV weight in the feedstock}} \times 100\%$$

selectivity (mole%) =

$$\frac{\text{PTE weight in the product} \times \text{molecular weight of FV/molecular weight of PTE}}{\text{mole of FV in the feedstock} - \text{mole of FV in the product}} \times 100\%$$

yield (mole%) =

$$\frac{\text{PTE weight in the product} \times \text{molecular weight o FV/moleculat weight of PTE}}{\text{mole of FV in the feedstock}} \times 100\%$$

The following examples are intended to illustrate the process and the advantages of the present invention more fully without limiting its scope, since numerous modifications and variations will be apparent to those skilled in the art.

EXAMPLE 1

130 g of aluminum hydroxide ($Al(OH)_3$), 17.5 g of calcium carbonate ($CaCO_3$), and 500 ml of deionized were mixed. 14 g of titania ($TiO_2$, titanium dioxide) was added slowly to the mixture under reflux at 100° C. to form a solution A. 20 g of silica ($SiO_2$) was added to 120 ml of deionized water and then 20 g of potassium hydroxide (KOH) was added. The mixture was stirred and heated to form a solution B.

The solution B was added to the solution A under reflux at 100° C. Then, 230 g of 85% $H_3PO_4$ solution was added at a rate of 18.3 g/min and the mixture was stirred at 100° C. for 8 hours. The solution was concentrated at 100° C. to give a sticky white product, which was then dried in an oven at 120° C. to give a solid white product. The solid white product was then cracked to form particles with a size of 30–40 mesh. Thus, a solid acid/base catalyst $Al_5Si_1Ca_{0.5}Ti_{0.5}P_6K_1O_x$ was obtained. 20 of the obtained solid acid/base catalyst and 30 ml of 0.05 M $Pd(NH_3)_4Cl_2$ solution (pH=10) were stirred for 1 hour. Then, the solution dried under reduced pressure, and calcined in the presence of air at 500° C. for 6 hours to give a pale yellow solid, that is, 1 wt %$Pd/Al_5Si_1Ca_{0.5}Ti_{0.5}P_6K_1O_x$, which can serve as a dehydrocarbonylation catalyst with selectivity.

7 ml of the obtained dehydrocarbonylation catalyst was placed in a ⅜" stainless steel tube to form a fixed bed reactor. Methyl formylvalerate, methanol, and water (33/57/10 in weight ratio) were mixed with the air and then charged from the upper portion of the reactor to the reactor at a liquid hour space velocity (LHSV) of 1 $hr^{-1}$. The fixed bed was controlled at 180° C. and the reactor was maintained at atmospheric pressure. After the reaction was completed, the reaction product was allowed to flow out from the reactor, cooled, and collected. The liquid product was analyzed by gas chromatography and the results are shown in Table 1.

TABLE 1

| | |
|---|---|
| Reaction temperature (° C.) | 180 |
| Feedstock composition (wt %) | |
| Formylvaleric ester | 33 |
| Methanol | 57 |
| Water | 10 |
| Molar ratio of oxygen/formylvaleric ester | 2.5 |
| Conversion of formylvaleric ester (%) | 92.55 |
| Selectivity of pentenoic ester (%) | 80.81 |

EXAMPLE 2

78 g of aluminum hydroxide, 19.8 g of magnesium nitrate ($Mg(NO_3)_2$), and 500 ml of deionized were mixed. 16 g of titania was added slowly to the mixture under reflux at 100° C. to form a solution A.

20 g of silica was added to 120 ml of deionized water and then 20 g of potassium hydroxide was added. The mixture was stirred and heated to form a solution B.

The solution B was added to the solution A under reflux at 100° C. Then, 192 g of 85% $H_3PO_4$ solution was added at a rate of 18.3 g/min and the mixture was stirred at 100° C. for 8 hours. The solution was concentrated at 100° C. to give a sticky white product, which was then dried in an oven at 120° C. to give a solid white product. The solid white product was then cracked to form particles with a size of 30–40 mesh. Thus, a solid acid/base catalyst $Al_3Si_1Mg_{0.4}Ti_{0.6}P_5K_1O_x$, was obtained.

20 of the obtained solid acid/base catalyst and 30 ml of 0.05 M $Pd(NH_3)_4Cl_2$ solution (pH=10) were stirred for 1 hour. Then, the solution dried under reduced pressure, and calcined in the presence of air at 500° C. for 6 hours to give a pale yellow solid, that is, 1 wt %Pd/ $Al_3Si_1Mg_{0.4}Ti_{0.6}P_5K_1O_x$, which can serve as a dehydrocarbonylation catalyst with selectivity.

7 ml of the obtained dehydrocarbonylation catalyst was placed in a ⅜" stainless steel tube to form a fixed bed reactor. Methyl formylvalerate, methanol, and water (33/57/10 in weight ratio) were mixed with the air and then charged from the upper portion of the reactor to the reactor at a liquid hour space velocity (LHSV) of 1 $hr^{-1}$. The fixed bed was controlled at 180° C. and the reactor was maintained at atmospheric pressure. After the reaction was completed, the reaction product was allowed to flow out from the reactor, cooled, and collected. The liquid product was analyzed by gas chromatography and the results are shown in Table 2.

TABLE 2

| | |
|---|---|
| Reaction temperature (° C.) | 180 |
| Feedstock composition (wt %) | |
| Formylvaleric ester | 33 |
| Methanol | 57 |
| Water | 10 |
| Molar ratio of oxygen/formylvaleric ester | 2.0 |
| Conversion of formylvaleric ester (%) | 90.76 |
| Selectivity of pentenoic ester (%) | 85.40 |

EXAMPLE 3–7

The procedures for preparing the catalyst were employed as described in Example 1. 7 ml of the obtained dehydrocarbonylation catalyst was placed in a ⅜" stainless steel tube to form a fixed bed reactor. Methyl formylvalerate, methanol, and water with various weight ratios were mixed with the air and then charged from the upper portion of the reactor to the reactor at various liquid hour space velocities (LHSV). The fixed bed was controlled at various temperature and the reactor was maintained at atmospheric pressure. After the reaction was completed, the reaction product was allowed to flow out from the reactor, cooled, and collected. The liquid product was analyzed by gas chromatography and the results are shown in Table 3.

TABLE 3

| Example | 3 | 4 | 5 | 6 | 7 |
|---|---|---|---|---|---|
| Reaction Condition | | | | | |
| Temperature (° C.) | 140 | 160 | 180 | 180 | 180 |
| LHSV (hr$^{-1}$) | 1 | 1 | 1.5 | 2 | 1 |
| Feedstock composition (wt %) | | | | | |
| FV | 23 | 23 | 23 | 23 | 33 |
| methanol | 67 | 67 | 67 | 67 | 59 |
| water | 10 | 10 | 10 | 10 | 8 |
| Molar ratio of oxygen/FV | 4.8 | 4.8 | 3.2 | 2.4 | 1.7 |
| Conversion of FV (%) | 74.15 | 67.40 | 76.51 | 74.71 | 80.57 |
| Selectivity of pentenoic ester (%) | 64.62 | 38.60 | 77.94 | 85.13 | 92.24 |

FV = formylvaleric ester

EXAMPLE 8

The procedures for preparing the catalyst were employed as described in Example 1. 50 ml of the obtained dehydrocarbonylation catalyst was placed in a 1" stainless steel tube to form a fixed bed reactor. Methyl formylvalerate, methanol, and water (33/59/8 in weight ratio) were mixed with the air and then charged from the upper portion of the reactor to the reactor at a liquid hour space velocity (LHSV) of 2 hr$^{-1}$. The fixed bed was controlled at 180° C. and the reactor was maintained at atmospheric pressure. After the reaction was completed, the reaction product was allowed to flow out from the reactor, cooled, and collected. The liquid product was analyzed by gas chromatography and the results are shown in Table 4.

TABLE 4

| | |
|---|---|
| Reaction temperature (° C.) | 180 |
| Feedstock Composition (wt %) | |
| formylvaleric ester | 33 |
| methanol | 59 |
| water | 8 |
| Molar ratio of oxygen/formylvaleric ester | 1.25 |
| Conversion of formylvaleric ester (%) | 90.43 |
| Selectivity of pentenoic ester (%) | 98.95 |
| 4-pentenoic ester | 42 |
| 3-pentenoic ester | 46 |
| 2-pentenoic ester and others | 12 |

From the above results, it can be seen that by means of the specific mixed oxide-supported noble metal as the catalyst according to the present invention, the formylvaleric ester has a high conversion, and the selectivity of the 3- and 4-pentenoic esters can be increased and that of the 2-pentenoic ester can be decreased to below 20%.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A process for preparing a pentenoic ester comprising heating a 3-, 4-formylvaleric ester or mixtures thereof at 50° C. to 400° C. in the presence of a supported noble metal catalyst,
   wherein the noble metal catalyst is supported on a mixed oxide $(M^1)_a(M^2)_b(M^3)_c P_d Al_e SiO_x$, wherein $M^1$ is an alkali metal, $M^2$ is an alkaline earth metal, $M^3$ is a Group IVB metal, a=0.5~1.5, b=0.2~0.8, c=0.2~0.8, d=2~8, e=3~10, and x is the stoichiometric value.

2. The process as claimed in claim 1, wherein $M^1$ is Li, Na, or K.

3. The process as claimed in claim 1, wherein $M^2$ is Be, Mg, or Ca.

4. The process as claimed in claim 1, wherein $M^3$ is Ti, Zr, or Hf.

5. The process as claimed in claim 1, wherein a=0.7~1.3, b=0.4~0.7, c=0.4~0.7, d=4~7, and e=4~8.

6. The process as claimed in claim 1, wherein the noble metal catalyst contains a Group VIIIB metal.

7. The process as claimed in claim 6, wherein the Group VIIIB metal is Pd, Pt, Rh, or Ru.

8. The process as claimed in claim 1, wherein the noble metal catalyst is present in an amount of 0.01 to 10 wt % based on the total weight of the noble metal catalyst and the mixed oxide.

9. The process as claimed in claim 8, wherein the noble metal catalyst is present in an amount of 0.1 to 5 wt % based on the total weight of the noble metal catalyst and the mixed oxide.

10. The process as claimed in claim 1, which is conducted at 100° C. to 250° C.

11. The process as claimed in claim 1, which is conducted in the presence of an oxygen-containing gas.

12. The process as claimed in claim 11, which is conducted in the presence of air.

13. The process as claimed in claim 11, which is conducted in the presence of oxygen.

14. The process as claimed in claim 1, wherein the 3- and 4-formylvaleric esters are independently an ester of alkyl having from 1 to 3 carbon atoms.

15. The process as claimed in claim 14, wherein methyl 3-formylvalerate and/or methyl 4-formylvalerate are used as the starting material.

16. The process as claimed in claim 1, wherein the formylvaleric ester has an LHSV of 0.1 to 10 $hr^{-1}$.

17. The process as claimed in claim 16, wherein the formylvaleric ester has an LHSV of 0.5 to 5 $hr^{-1}$.

* * * * *